(12) United States Patent
Hoarau et al.

(10) Patent No.: US 9,089,329 B2
(45) Date of Patent: Jul. 28, 2015

(54) ENGAGEMENT DEVICE AND METHOD FOR DEPLOYMENT OF ANASTOMOTIC CLIPS

(71) Applicants: Carine Hoarau, Lafayette, CA (US); Steven H. Reichenbach, Pleasanton, CA (US); George Hsu, San Ramon, CA (US); James N. Harrington, Pleasanton, CA (US); Andrew R. Miller, The Woodlands, TX (US); Philip Haarstad, Chanhassen, MN (US); Stephen Kenneth Sundquist, Minnetonka, MN (US)

(72) Inventors: Carine Hoarau, Lafayette, CA (US); Steven H. Reichenbach, Pleasanton, CA (US); George Hsu, San Ramon, CA (US); James N. Harrington, Pleasanton, CA (US); Andrew R. Miller, The Woodlands, TX (US); Philip Haarstad, Chanhassen, MN (US); Stephen Kenneth Sundquist, Minnetonka, MN (US)

(73) Assignee: Thoratec Corporation, Pleasanton, CA (US)

( * ) Notice: Subject to any disclaimer, the term of this patent is extended or adjusted under 35 U.S.C. 154(b) by 38 days.

(21) Appl. No.: 13/839,387

(22) Filed: Mar. 15, 2013

(65) Prior Publication Data
US 2013/0282026 A1    Oct. 24, 2013

Related U.S. Application Data

(60) Provisional application No. 61/636,889, filed on Apr. 23, 2012.

(51) Int. Cl.
*A61B 17/10* (2006.01)
*A61B 17/11* (2006.01)
(Continued)

(52) U.S. Cl.
CPC ............... *A61B 17/11* (2013.01); *A61B 17/115* (2013.01); *A61B 17/0644* (2013.01);
(Continued)

(58) Field of Classification Search
CPC .......................... A61B 17/1285; A61B 17/122
USPC ......... 606/151, 153–156, 139, 142, 143, 150; 623/1.11, 1.23; 227/175.1, 179.1, 19
See application file for complete search history.

(56) References Cited

U.S. PATENT DOCUMENTS 5,158,563 A    10/1992 Cosman
5,291,179 A    3/1994 Ooe et al.
(Continued)

FOREIGN PATENT DOCUMENTS

DE    10 2004 047974    4/2006
EP    1 691 884 B1    3/2011
(Continued)

OTHER PUBLICATIONS

International Search Report for PCT/US2010/056751, mailed Oct. 7, 2011, 22 pgs.
(Continued)

*Primary Examiner* — Todd Manahan
*Assistant Examiner* — Erich Herbermann
(74) *Attorney, Agent, or Firm* — Squire Patton Boggs (US) LLP

(57) ABSTRACT

A coupling system includes an applicator tool, an anastomotic prosthesis mounted on the applicator tool, and an engagement device. The applicator tool deploys a securement through the prosthesis and tissue which leaves the prosthesis attached to the tissue. The engagement device selectively engages the applicator tool onto the tissue, with the use of suction, in order to facilitate accurate placement of the prosthesis on the tissue and facilitate deployment of the securement into the tissue. The applicator tool and the tissue are able to move together while the engagement device prevents or inhibits relative movement between the applicator tool and the tissue. A method for securing an anastomotic prosthesis to tissue includes applying of suction to engage an applicator tool to the tissue while a securement is deployed out of the applicator tool and into the prosthesis and the tissue.

12 Claims, 17 Drawing Sheets

(51) Int. Cl.
*A61B 17/115* (2006.01)
*A61B 17/064* (2006.01)
*A61B 17/00* (2006.01)
*A61B 17/30* (2006.01)
*A61B 19/00* (2006.01)

(52) U.S. Cl.
CPC ............... *A61B 2017/00252* (2013.01); *A61B 2017/00867* (2013.01); *A61B 2017/0647* (2013.01); *A61B 2017/1107* (2013.01); *A61B 2017/308* (2013.01); *A61B 2019/521* (2013.01)

(56) References Cited

U.S. PATENT DOCUMENTS

| | | |
|---|---|---|
| 5,582,616 A | 12/1996 | Bolduc et al. |
| 5,814,005 A | 9/1998 | Barra et al. |
| 5,827,316 A | 10/1998 | Young et al. |
| 6,079,414 A | 6/2000 | Roth |
| 6,080,173 A | 6/2000 | Williamson, IV et al. |
| 6,113,611 A | 9/2000 | Allen et al. |
| 6,193,652 B1 * | 2/2001 | Berky et al. .................. 600/205 |
| 6,346,071 B1 | 2/2002 | Mussivand |
| 6,511,416 B1 * | 1/2003 | Green et al. .................. 600/37 |
| 6,537,300 B2 | 3/2003 | Girton |
| 6,551,332 B1 | 4/2003 | Nguyen et al. |
| 6,607,541 B1 | 8/2003 | Gardiner et al. |
| 6,669,708 B1 | 12/2003 | Nissenbaum et al. |
| 6,689,147 B1 | 2/2004 | Koster, Jr. |
| 6,695,859 B1 | 2/2004 | Golden et al. |
| 6,699,256 B1 | 3/2004 | Logan et al. |
| 6,726,648 B2 | 4/2004 | Kaplon et al. |
| 6,732,501 B2 | 5/2004 | Yu et al. |
| 6,802,806 B2 | 10/2004 | McCarthy et al. |
| 6,824,071 B1 | 11/2004 | McMichael |
| 6,863,677 B2 | 3/2005 | Breznock |
| 6,942,672 B2 | 9/2005 | Heilman et al. |
| 7,077,801 B2 | 7/2006 | Haverich |
| 7,309,343 B2 | 12/2007 | Vargas et al. |
| 7,431,727 B2 * | 10/2008 | Cole et al. .................. 606/153 |
| 7,510,561 B2 | 3/2009 | Beane et al. |
| 7,717,844 B2 | 5/2010 | Cohn |
| 7,744,527 B2 | 6/2010 | Cohn |
| 7,846,123 B2 | 12/2010 | Vassiliades et al. |
| 7,931,581 B2 | 4/2011 | Cohn |
| 7,942,805 B2 | 5/2011 | Shambaugh, Jr. |
| 7,993,392 B2 | 8/2011 | Righini et al. |
| 8,226,670 B2 | 7/2012 | Beane et al. |
| 8,556,930 B2 | 10/2013 | Ellingwood |
| 2002/0045846 A1 | 4/2002 | Kaplon et al. |
| 2003/0023255 A1 | 1/2003 | Miles et al. |
| 2003/0130668 A1 | 7/2003 | Neiman et al. |
| 2004/0049194 A1 | 3/2004 | Harvie et al. |
| 2004/0087985 A1 * | 5/2004 | Loshakove et al. ........... 606/153 |
| 2004/0092798 A1 | 5/2004 | Spence et al. |
| 2004/0102794 A1 | 5/2004 | Roy et al. |
| 2005/0187568 A1 | 8/2005 | Klenk et al. |
| 2005/0228410 A1 * | 10/2005 | Berreklouw .................. 606/153 |
| 2005/0251209 A1 | 11/2005 | Saadat et al. |
| 2006/0036313 A1 | 2/2006 | Vassiliades et al. |
| 2006/0074484 A1 | 4/2006 | Huber |
| 2006/0089707 A1 | 4/2006 | Vassiliades et al. |
| 2006/0167333 A1 | 7/2006 | Moore et al. |
| 2007/0055357 A1 | 3/2007 | Pokorney et al. |
| 2007/0066943 A1 | 3/2007 | Prasad et al. |
| 2007/0106315 A1 | 5/2007 | Gregoric et al. |
| 2007/0112384 A1 | 5/2007 | Conlon et al. |
| 2007/0167964 A1 * | 7/2007 | Willis .......................... 606/153 |
| 2007/0167969 A1 | 7/2007 | Pandey |
| 2007/0197856 A1 | 8/2007 | Gellman et al. |
| 2007/0265643 A1 | 11/2007 | Beane et al. |
| 2008/0300628 A1 | 12/2008 | Ellingwood |
| 2009/0112062 A1 | 4/2009 | Bakos |
| 2009/0171136 A1 | 7/2009 | Shambaugh, Jr. |
| 2009/0204206 A1 | 8/2009 | Parquet et al. |
| 2009/0302089 A1 | 12/2009 | Harari et al. |
| 2010/0010500 A1 | 1/2010 | Beane et al. |
| 2010/0010538 A1 | 1/2010 | Juravic et al. |
| 2010/0161040 A1 | 6/2010 | Braido et al. |
| 2010/0168778 A1 | 7/2010 | Braido |
| 2010/0211082 A1 | 8/2010 | Sauer |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2012/0089181 A1 | 4/2012 | Shanley et al. |
| 2012/0165931 A1 | 6/2012 | Bourque |
| 2012/0221021 A1 | 8/2012 | Hoarau et al. |

FOREIGN PATENT DOCUMENTS

| | | |
|---|---|---|
| EP | 1 628 702 B1 | 5/2013 |
| WO | WO 96/03925 | 2/1996 |
| WO | WO 96/25886 | 8/1996 |
| WO | WO 03/001980 | 1/2003 |
| WO | WO 2006/019755 | 2/2006 |
| WO | WO 2007/038109 | 4/2007 |
| WO | WO 2008/153872 A2 | 12/2008 |
| WO | WO 2009/100198 | 8/2009 |
| WO | WO 2013/064529 A1 | 5/2013 |

OTHER PUBLICATIONS

International Search Report for PCT/US2012/026838, mailed Aug. 10, 2012, 9 pgs.

International Search Report for PCT/US2013/031279, mailed Jul. 10, 2013, 14 pgs.

International Search Report and Written Opinion for PCT/US2014/029703, mailed Jul. 17, 2014, 14 pgs.

* cited by examiner

ENGAGEMENT DEVICE AND METHOD FOR DEPLOYMENT OF ANASTOMOTIC CLIPS

CROSS-REFERENCE TO RELATED APPLICATION

This application claims the benefit of U.S. Provisional Application No. 61/636,889, filed Apr. 23, 2012, which is incorporated herein by reference for all purposes.

FIELD OF THE INVENTION

The invention relates to a surgical device and method, and more particularly, a device and method for engagement to biological tissue during deployment of anastomotic clip or other securements.

BACKGROUND OF THE INVENTION

Surgical procedures for connecting an anastomotic prosthesis to biological tissue, such as a blood vessel and the heart, have required manually suturing the prosthesis to the tissue. Manual suturing can be difficult due to limited access to, location of, and/or type of tissue. As an alternative or a compliment to manual suturing, an applicator tool can be used to deploy clips, sutures, and/or other types of securement for connecting the prosthesis to the tissue. The applicator tool can be used during minimally invasive surgery. During one type of minimally invasive surgery, a small hole or port may be created through the patient's body to give the surgeon access from outside of the body into a body cavity. The surgeon can have limited visibility of the target site and limited space for operation. Thus, the applicator tool can help to connect the surgeon to this target site and provide a constant connection with the target site to perform the targeted procedure.

When using an applicator tool, tissue may shift in position and/or move away from the applicator tool, which makes it difficult to accurately place the prosthesis at the desired location and to deploy the securement into the tissue. For example, when the tissue is a blood vessel or the heart, pulsatile blood flow may cause the tissue to shift in position. Even when blood flow is temporarily blocked or bypassed, the wet and slippery tissue may be pushed away instead of being pierced by the securement being deployed by the applicator tool. Even if surrounding tissue is secured, such as with temporary sutures, to a fixed structure like a surgical bed or a sternum retractor used to hold open the chest cavity, the tissue and applicator tool may still move relative to each other while the applicator tool is held by the surgeon. Relative movement between the tissue and applicator tool can cause inaccurate deployment of securement by the applicator tool.

There is a continuing need to make the procedure for connecting a prosthesis to tissue easier and faster to perform. There is also a need to engage an applicator tool to tissue during deployment of securement by an applicator tool.

SUMMARY OF THE INVENTION

Briefly and in general terms, the present invention is directed a coupling system and method for connecting an anastomotic prosthesis to tissue.

In aspects of the present invention, a system comprises an applicator tool configured to deploy a securement into an anastomotic prosthesis and tissue, and an engagement device attached to the applicator tool and configured to selectively engage and disengage the applicator tool to tissue.

In other aspects, the engagement device is configured to engage the tissue with application of suction to the engagement device, and is configured to disengage the tissue with removal of the suction.

In other aspects, the engagement device includes a plurality of contact members, each contact member including a concave wall, the concave wall having an aperture through which suction can be applied.

In other aspects, the engagement device includes a fluid conduit coupled to the apertures through which suction can be applied.

In other aspects, the engagement device includes a coupling member to which the contact members are attached, the coupling member sized to receive a forward segment of the applicator tool.

In other aspects, the coupling member is slideably coupled to the forward segment of the applicator tool.

In other aspects, the system further comprises an attachment ring for connecting an artificial conduit to a hollow anatomical organ.

In other aspects, the attachment ring is configured to connect an inflow conduit of a ventricular assist device to a heart.

In other aspects, the applicator tool includes a connector mechanism configured to selectively hold and release the attachment ring, and the applicator tool is configured to deploy the securement into the attachment ring.

In other aspects, the securement is a clip having a sharp tip for piercing the tissue.

In aspects of the present invention, a method comprises applying suction to an engagement device attached to an applicator tool. The applicator tool is configured to deploy a securement into an anastomotic prosthesis and the tissue. The method further comprises deploying the securement into the anastomotic prosthesis and the tissue during the applying of the suction to the engagement device.

In other aspects, the method further comprises removing the suction from the engagement device after the deploying of the securement, wherein the applying of the suction causes the engagement device to engage the tissue, and the removing of the suction causes the engagement device to disengage the tissue.

In other aspects, the applying of the suction to the engagement device includes applying the suction to a plurality of contact members disposed on the tissue, each contact member including a concave wall, the concave wall having an aperture through which suction is applied.

In other aspects, the suction is applied through a fluid conduit coupled to the apertures.

In other aspects, the method further comprises placing a forward segment of the applicator tool in a coupling member, the contact members being attached to the coupling member.

In other aspects, the method further comprises adjusting an axial position of the contact members by sliding the coupling member on the forward segment of the applicator tool.

In other aspects, the anastomotic prosthesis is an attachment ring for connecting an artificial conduit to a hollow anatomical organ, and the method further comprises positioning the attachment ring on the hollow anatomical organ before applying the suction to the engagement device.

In other aspects, the method further comprises connecting an inflow conduit of a ventricular assist device to the attachment ring.

In other aspects, the positioning of the attachment ring on the tissue is performed while the attachment ring is mounted on the applicator tool, and the method further comprises releasing the attachment ring from the applicator tool after the deploying of the securement.

In other aspects, the securement is a clip having a sharp tip for piercing the tissue.

The features and advantages of the invention will be more readily understood from the following detailed description which should be read in conjunction with the accompanying drawings.

DETAILED DESCRIPTION OF THE PREFERRED EMBODIMENTS

As used herein, the term "anastomosis" refers to the interconnection of two hollow structures, any of which can be an artificial tubular conduit, a blood vessel, a heart, or other hollow anatomical organ. For example and without limitation, anastomosis can be performed to connect an inflow conduit of a ventricular assist device (VAD) to the ventricular apex of the heart. Various types of VADs are known in the art and need not be discussed herein. A feature or structure modified by the term "anastomotic" means that the feature or structure relates to or is used during interconnection of two hollow structures.

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. For example and without limitation, a first structure that is described as "substantially parallel" in reference to a second structure encompasses an orientation that is perfectly parallel and an orientation that one skilled in the art would readily recognize as being parallel even though distances between corresponding locations on the two respective structures are not exactly the same.

As used herein, a "through-hole" refers to a lumen that extends from one surface of a structure completely through the structure to another surface of the structure such that, if desired, a fluid could pass completely through the structure.

Figure 1:
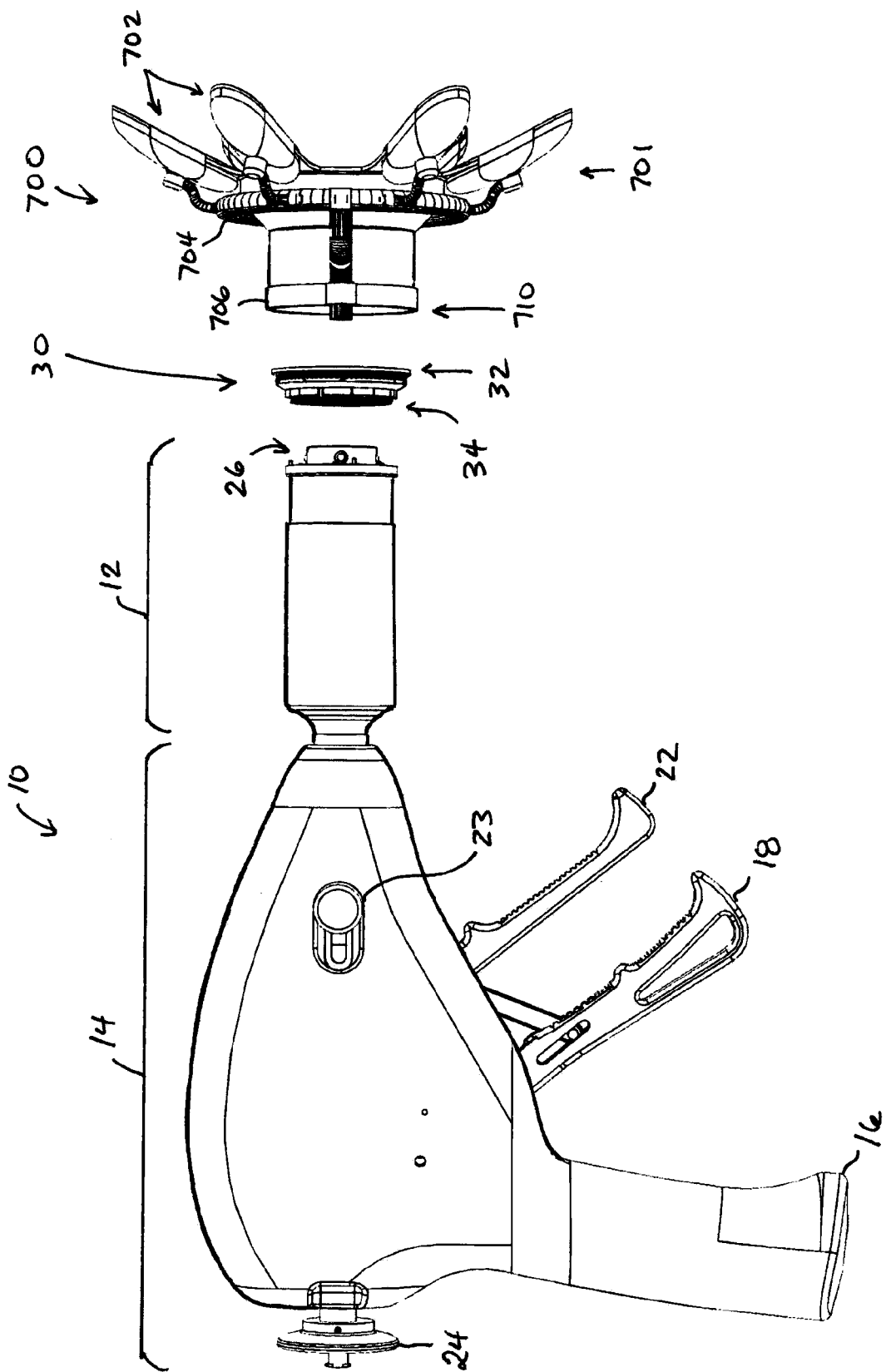
FIG. 1 is a disassembled, side view of an exemplary coupling system for securing an anastomotic prosthesis to biological tissue, showing an applicator tool, an attachment ring, and an engagement device.
Figure 2:
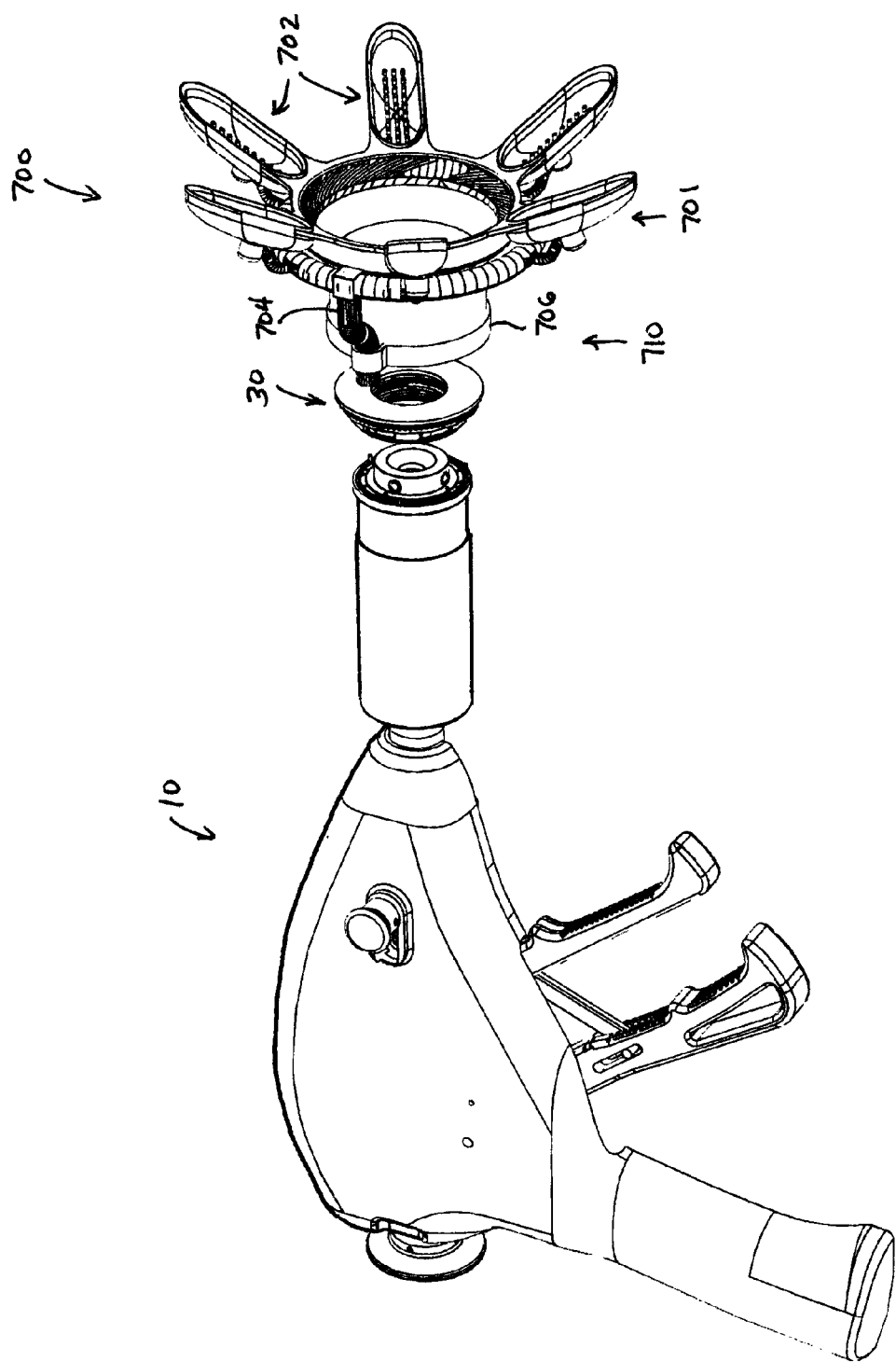
FIG. 2 is a disassembled, perspective view of the coupling system of FIG. 1.
Figure 3:
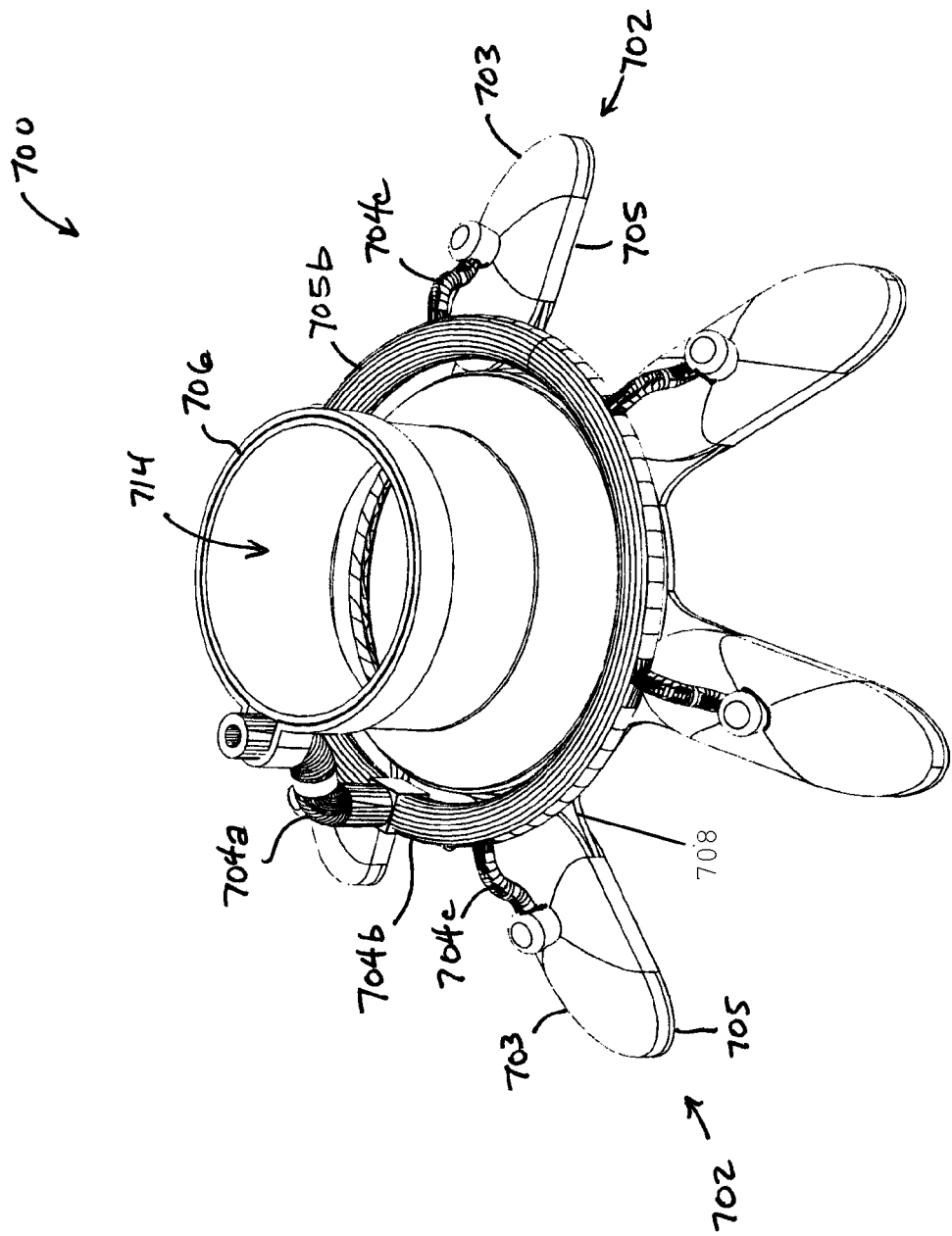
FIGS. 3-6 are perspective, top, bottom, and side views of the engagement device of FIG. 1.
Figure 4:
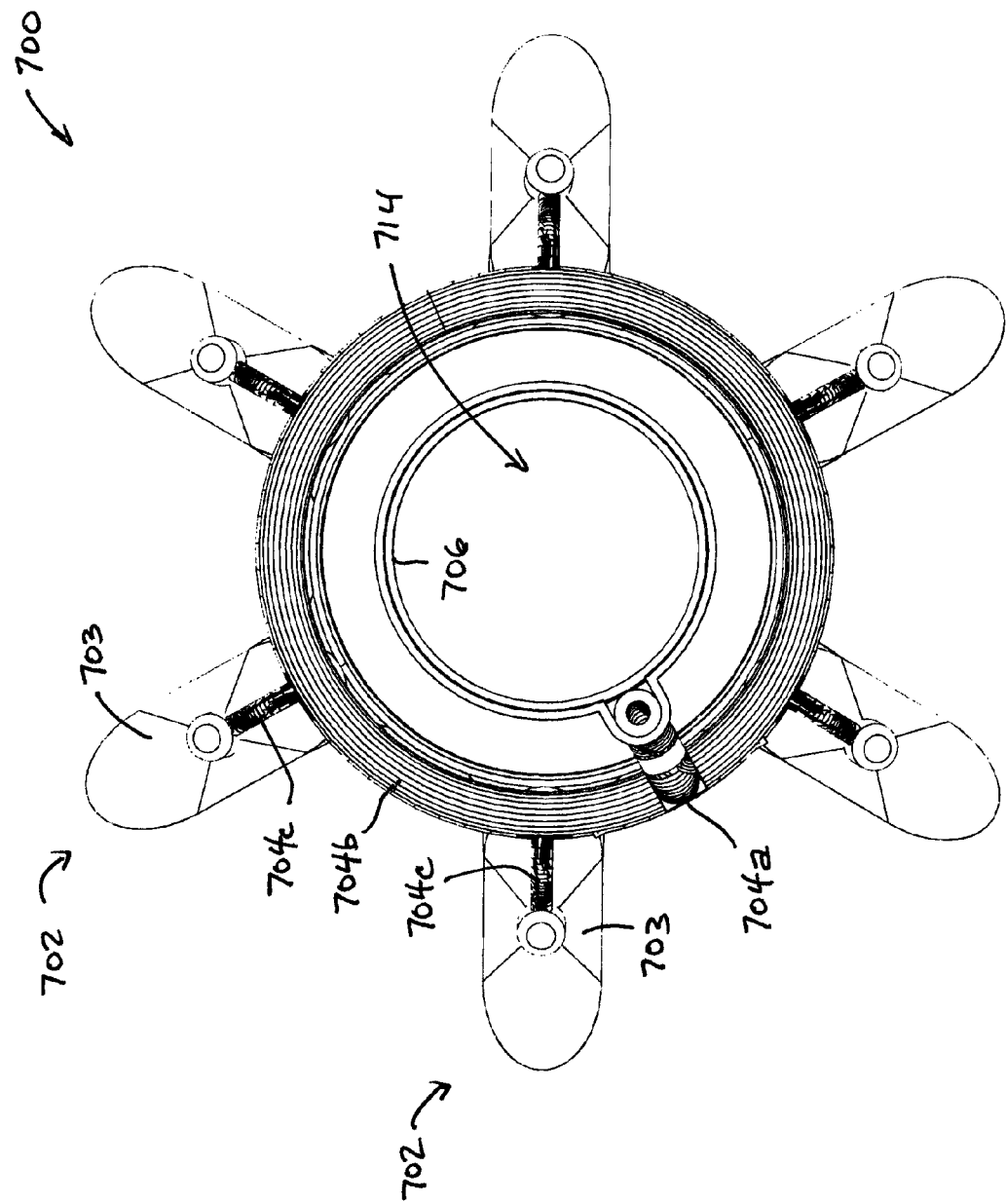
Figure 5:
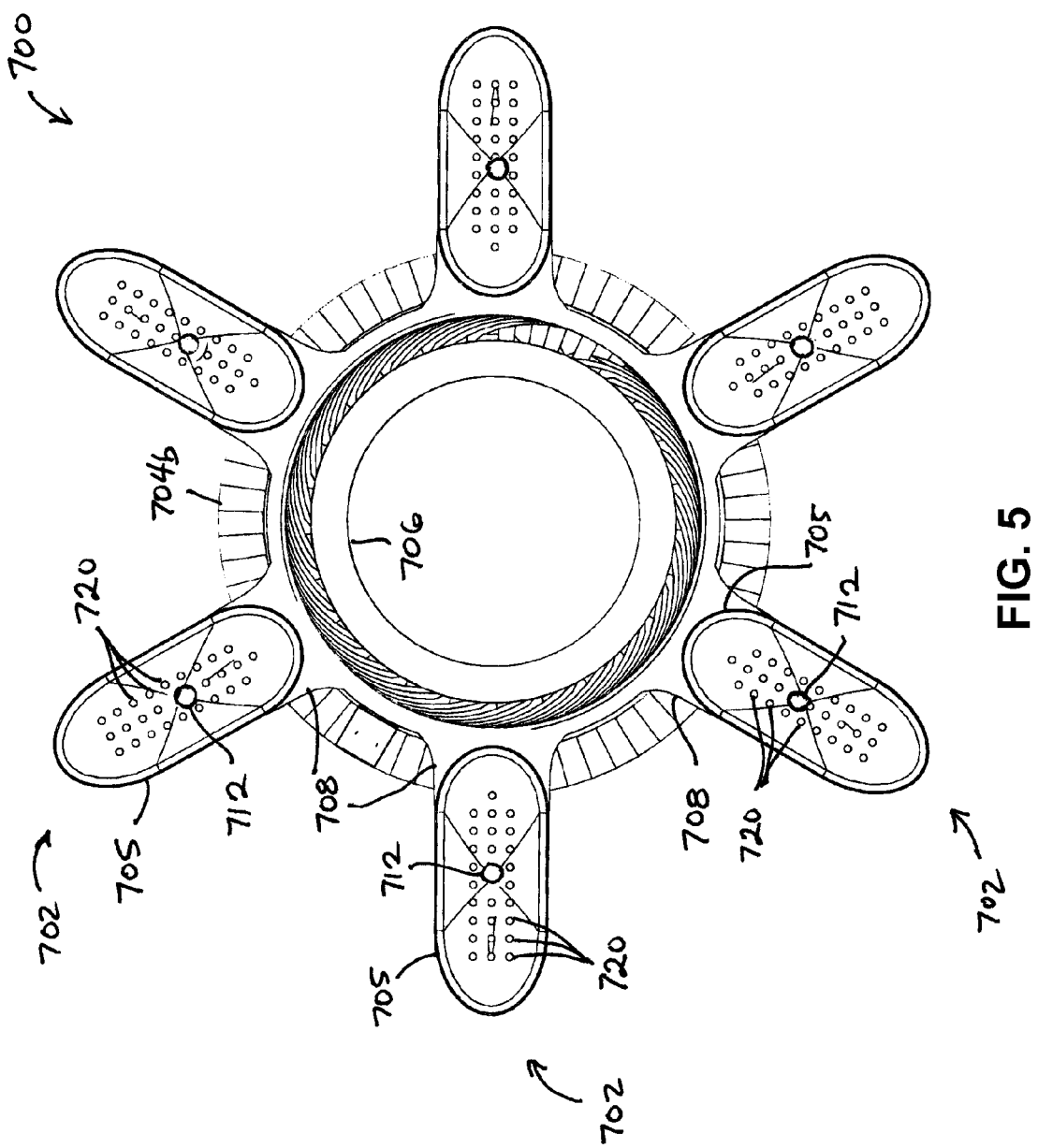

Referring now in more detail to the exemplary drawings for purposes of illustrating embodiments of the invention, wherein like reference numerals designate corresponding or like elements among the several views, there is shown in FIGS. 1 and 2 applicator tool 10 for anchoring attachment ring 30 to biological tissue. Attachment ring 30 is a type of anastomotic prosthesis suitable for implantation within a human or animal body. Attachment ring 30 is a coupling for a conduit, graft, or other structure that is to be connected to a hollow anatomical organ. Forward segment 12 of applicator tool 10 is configured to engage attachment ring 30. Rear segment 14 has grip 16. Clip deployment handle 18, cinching handle 22, release knob 23, and disengagement knob 24 are used to control various elements in forward segment 12.

Attachment ring 30 has bottom end 32 and top end 34. Bottom end 32 is secured to biological tissue and top end 34 is configured to engage forward segment 12 of applicator tool 10. In some embodiments, attachment ring 30 includes features configured to connect with a conduit, such as an inflow conduit of a ventricular assist device (VAD), after attachment ring 30 has been secured to biological tissue, such as the ventricular apex of the heart. Methods for securing an inflow conduit to the ventricular apex by means of an attachment ring are described in U.S. Application Publication Nos. 2011/0118766 A1, 2011/0118833 A1, and 2011/0118829 A1, which are incorporated herein by reference for all purposes.

In use, attachment ring 30 is engaged to and carried by connector mechanism 26 at forward segment 12 of applicator tool 10. The user positions forward segment 12 at the desired location on biological tissue where attachment ring 30 is to be secured. The user actuates the various controls on applicator tool 10 to simultaneously deploy multiple clips, or other type of anastomotic securements, that secure attachment ring 30 to the tissue and to disconnect connector mechanism 26 from attachment ring 30.

In some embodiments, when the user actuates clip deployment handle 18, clips are pushed out of applicator tool 10 such that the tips of clips pass through attachment ring 30 and into underlying tissue. The tips initially move downward in a substantially straight trajectory into the tissue. Thereafter, each tip follows a curved trajectory that extends radially outward and away from attachment ring 30 and returns upward out of the tissue. The tips then turn downward and return toward attachment ring 30 and stop at a position adjacent to or on an outer surface of attachment ring 30. Thus it will be understood that during deployment out of applicator tool 10, the clips pass through and curl back toward attachment ring 30. As the user continues to pull clip deployment handle 18, a portion of attachment ring 30 clamps down onto or traps the tips, and prevents the tips from moving backwards into the tissue. Next, as the user actuates cinching handle 22, the rear segment of each clip is pulled up away from the tissue and into applicator tool 10. Since the tip of each clip is held in place by attachment ring 30, pulling the rear segment of each clip causes the middle segment of each clip to cinch or tighten against the tissue. This tightening of the clips increases engagement between the tissue and attachment ring 30. When the user actuates release knob 23, the rear segment of each clip is released from applicator tool 10. Features on each clip and attachment ring 30, such as protrusions and catch features, prevent the rear segment of each clip from slipping or moving down toward the tissue, which maintains the cinched or tightened state of the clips. When the user actuates disengagement knob 24, attachment ring 30 is released by connector mechanism 26 of applicator tool 10, which allows applicator tool 10 to be pulled away from the tissue while attachment ring 30 remains attached to the tissue.

In use, engagement device 700 is fitted around and engaged to forward segment 12 of applicator tool 10. Engagement device 700 is configured to temporarily engage forward segment 12 of applicator tool 10 to biological tissue to facilitate accurate positioning of attachment ring 30 to the tissue and to facilitate deployment of clips into the tissue. Engagement device 700 is configured to selectively engage onto and disengage from the tissue with the application and removal of suction. Engagement device 700 is set to engage onto tissue, with application of suction, when clips are deployed and cinched by applicator tool 10. Engagement device 700 is set to disengage from the tissue, with a partial decrease or complete removal of suction, after the clips are deployed and before applicator tool 10 is pulled away from the tissue and attachment ring 30.

As shown in FIGS. 3-8 engagement device 700 includes a plurality of contact members 702, a fluid conduit 704, and coupling member 706. Contact members 702 are disposed at bottom or forward end 701 (FIG. 6) of engagement device 700. Each contact member 702 includes concave wall 703 forming a cup-shape. Concave wall 703 becomes thinner in thickness toward peripheral edge 705. Peripheral edge 705 of concave wall 703 is configured to conform to curvature at the surface of biological tissue. Each contact member 702 is attached by flexible joint 708 to coupling member 706 to accommodate tissue surface curvature. Concave wall 703 and joint 708 can be made of silicone rubber or other resilient material. In use, peripheral edges 705 will seal against biological tissue to maintain negative pressure and suction within the interior cavity enclosed by concave walls 703 of each contact member 702.

Fluid conduit 704 is a tube that extends from top or rear end 710 (FIG. 6) of engagement device 700, and connects to suction aperture 712 (FIG. 5) formed through concave walls 703 of each contact member 702. Fluid conduit 704 is configured to convey suction to and draw air out of the interior cavity of each contact member 702.

Fluid conduit 704 includes rear tube 704a, ring tube 704b, and a plurality of forward tubes 704c. Rear tube 704a is configured to be connected to a negative pressure source or suction pump. An end of rear tube 704a is connected to ring tube 704b which is connected to ends of forward tubes 704c. The opposite end of forward tubes 704c are connected to suction apertures 712 (FIG. 5) in concave walls 703 of contact members 702. The lumen of rear tube 704a, ring tube 704b, and forward tubes 704c are interconnected so that any negative pressure, vacuum, or suction applied to rear tube 704a is fluidly communicated to the interior cavity of each contact member 702. When peripheral edges 705 of contact members 702 are disposed on the surface of tissue, contact members 702 engage and maintain hold of the tissue so as to prevent or minimize relative movement between applicator tool 10 and the tissue.

Coupling member 706 is in the shape of a tube and has central lumen 714. Central lumen 714 is sized to receive forward segment 12 of applicator tool 10. Six contact members 702 are arranged circumferentially around central lumen 714 at substantially equal circumferential spacing of about 60 degrees. In other embodiments, an engagement device can include a lesser or greater number of contact members 702.

Figure 6:
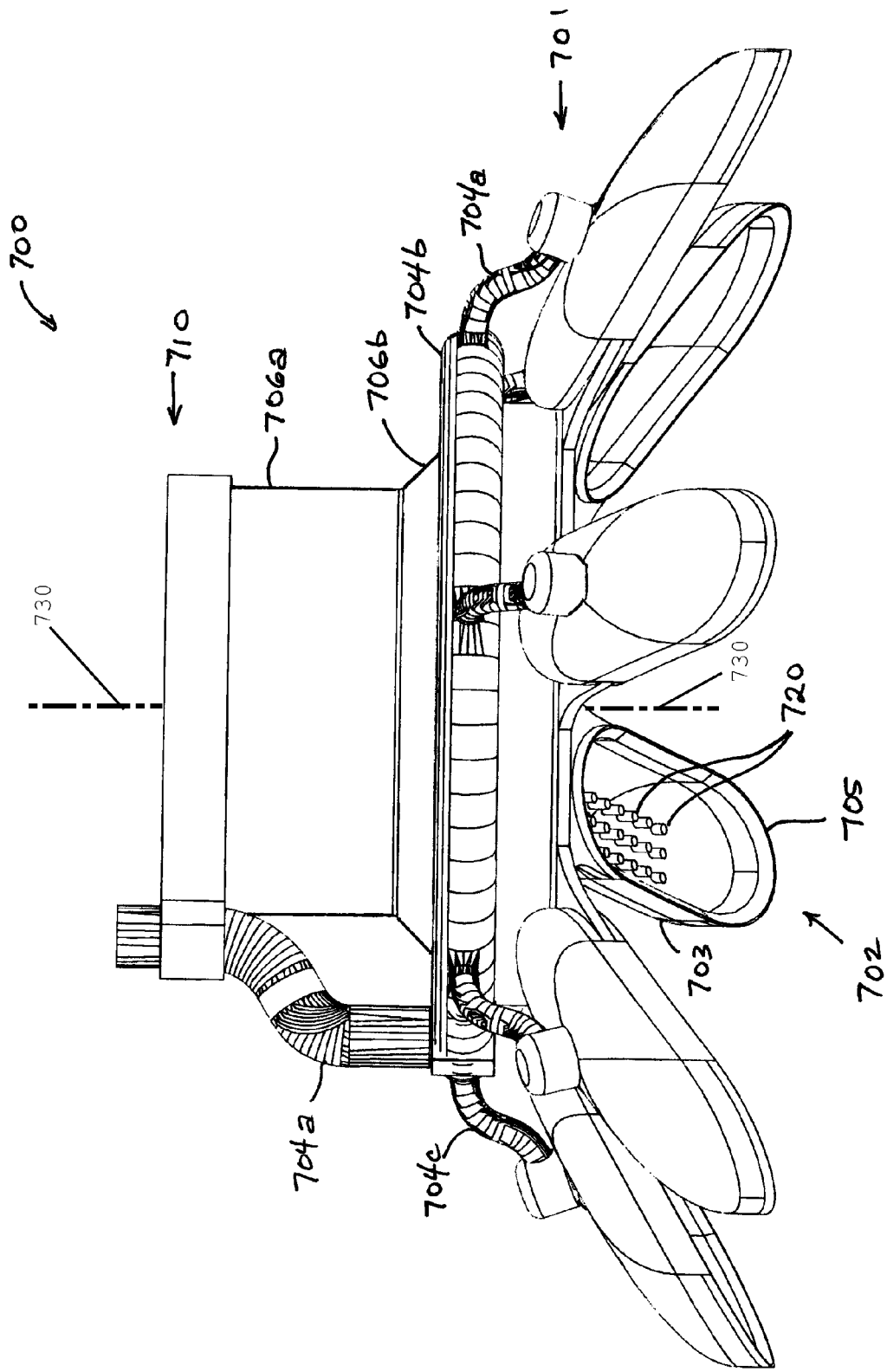
Figure 7:
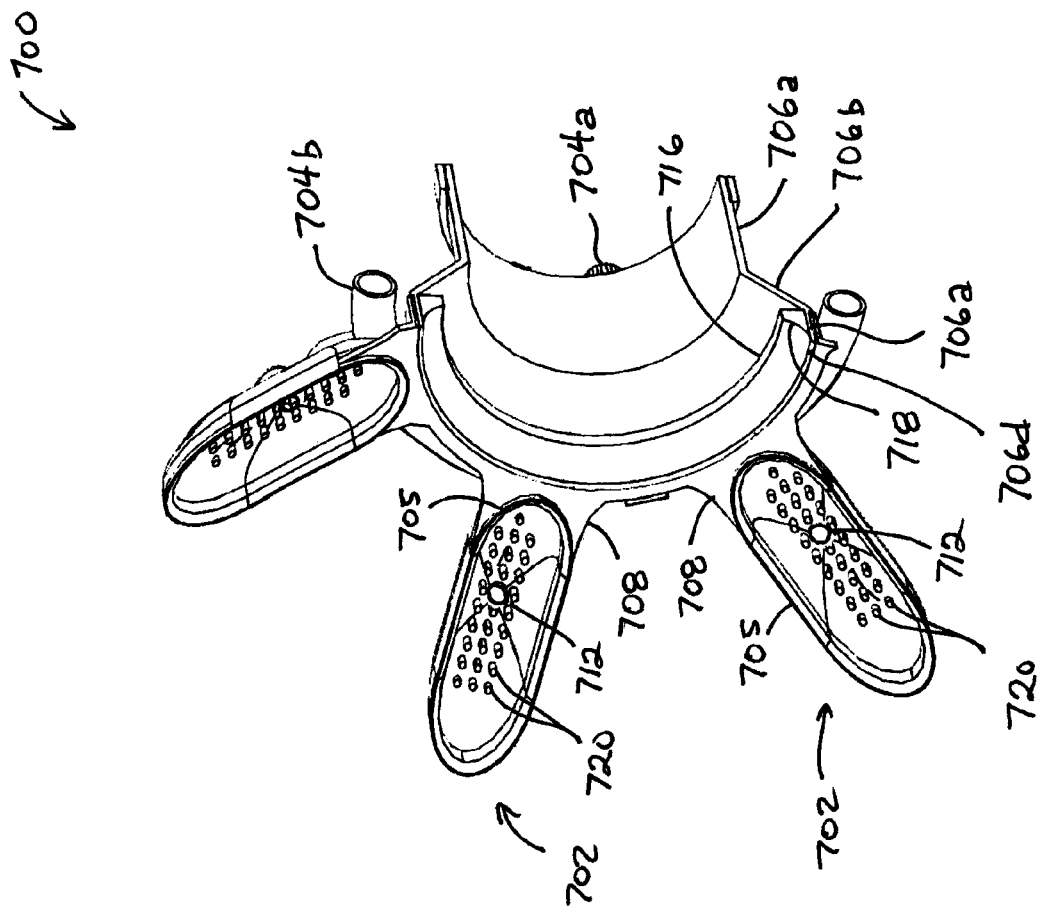
FIGS. 7 and 8 are cross-section views of the engagement device of FIG. 1, showing the engagement device in perspective and from the side.
Figure 8:
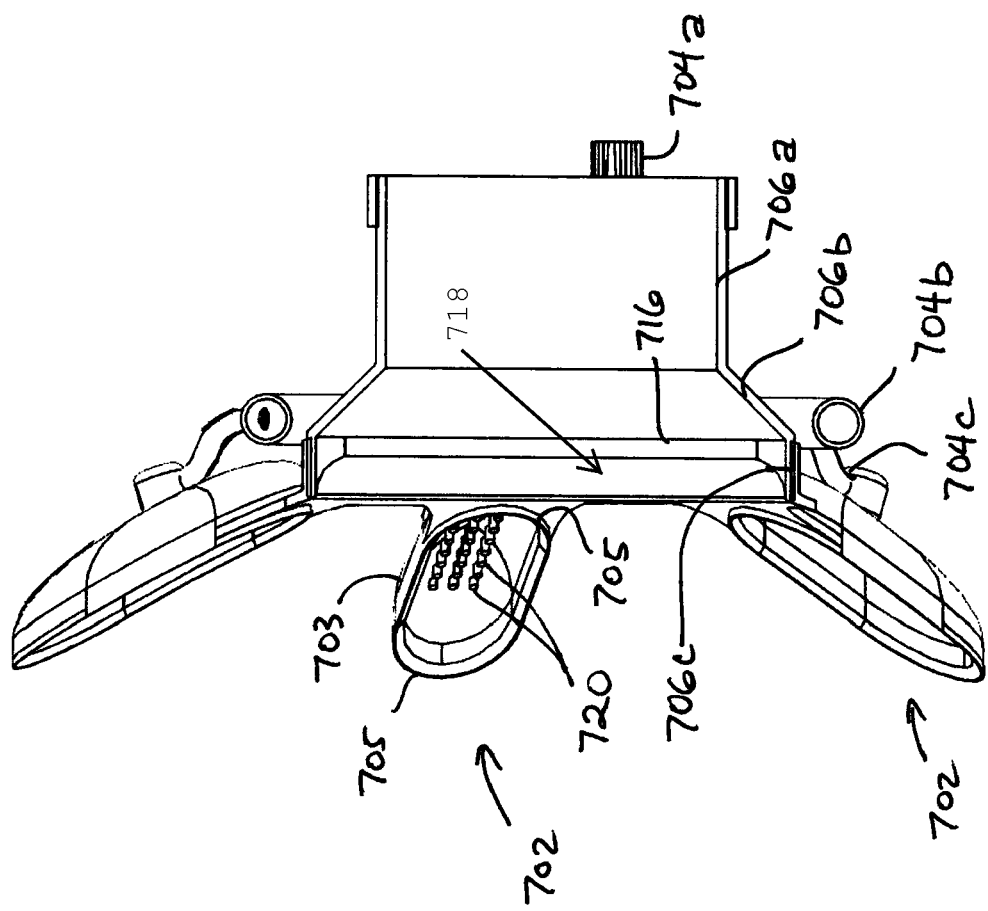

Referring to FIGS. 6-8, coupling member 706 includes narrow portion 706a at rear end 710, flared portion 706b, and wide portion 706c at forward end 701. Flared portion 706b extends radially outward from narrow portion 706a. Flared portion 706b connects narrow portion 706a to wide portion 706c. In use, narrow portion 706a is attached to forward segment 12 of applicator tool 10. Narrow portion 706a, flared portion 706b, and wide portion 706c can be formed of a substantially transparent or translucent material, such as a clear polycarbonate polymer, to allow the user to see underlying biological tissue and placement of attachment ring 30 on the tissue.

As shown in FIGS. 7 and 8, the exterior surface of wide portion 706c is attached by flexible joints 708 to contact members 702. The interior surface of wide portion 706c is attached to guide ring 716. Guide ring 716 is disposed within wide portion 706c. Guide ring 716 includes a smooth, annular surface 718 that slopes and curves radially inward as it extends rearward away from forward edge 706d of wide portion 706c. Annular surface 718 helps to insure radial inward travel of tips of securement that are deployed out of applicator tool 10.

As shown in FIGS. 5-8, each contact member 702 includes a plurality of protrusions 720 in the form of cylindrical posts attached to the interior surface of concave walls 703. Protrusions 720 surround suction aperture 712 and can help maintain a large area of suction and/or increase frictional engagement with biological tissue.

In some embodiments, concave walls 703 may be made of a flexible material, such as silicone rubber, to facilitate formation of a seal between peripheral edge 705 and the surface of tissue. As negative pressure builds in the cavity between concave walls 703 and the tissue surface, concave walls 703 may tend to collapse toward the tissue surface. Such collapse may result in deformation of peripheral edges 705 that causes loss of the air seal between peripheral edges 705 and the tissue. Also, if suction aperture 712 contacts tissue surface, suction and thus the area of tissue surface engagement will be limited to the area immediately surrounding suction aperture 712. Protrusions 720 are configured to help maintain the air seal and to prevent suction aperture 712 from contacting the tissue surface so that the area of tissue surface engagement extends out to peripheral edges 705 of contact members 702.

In some embodiments, protrusions 720 are configured to provide frictional engagement against the tissue surface. As negative pressure builds in the cavity between concave walls 703 and the tissue surface, concave walls 703 may tend to collapse toward the tissue surface so that protrusions 720 presses against and frictionally engage the tissue surface.

Figure 9:
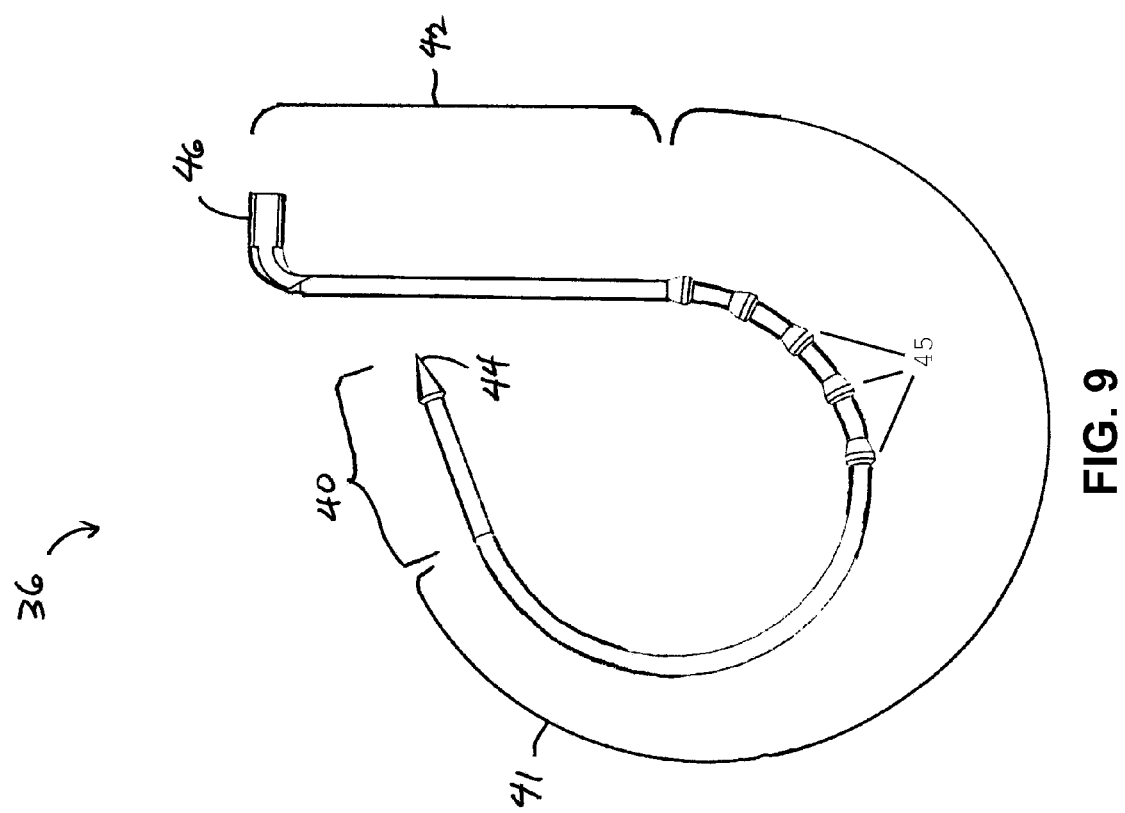
FIG. 9 is a plan view of a clip which can be carried within and deployed out of the applicator tool of FIG. 1.

The clips for anchoring attachment ring 30 to biological tissue are contained within forward segment 12 of applicator tool 10. The configuration of each clip can be as shown in FIG. 9. Clip 36 is formed from a metal wire made of a nickel-titanium alloy, Nitinol, or other material having shape memory and/or superelastic properties. Clip 36 includes forward segment 40 and rear segment 42, both of which are substantially straight. Forward segment 40 has sharp tip 44 for piercing a portion of attachment ring 30 and underlying biological tissue. Catch 46 protrudes out from rear segment 42 and is pushed forward (deployment) and pulled backward (cinching) during operation of applicator tool 10. Curved segment 41 connects forward segment 40 to rear segment 42. Curved segment includes a plurality of studs or bumps 45 that protrude radially outward. After clips 36 are cinched, the bumps 45 prevent the clips moving forward due to tension. Each bump 45 allows for a different amount of cinching to accommodate variations in the thickness of biological tissue. Bumps 45 can be shaped and sized to engage one or more structural catch features of attachment ring 30 to inhibit or prevent clip 36 from loosening after being cinched.

When loaded inside applicator tool 10, curved segment 41 is in a straightened configuration. When deployed out of applicator tool 10, tip 44 will initially follow a straight path through attachment ring 30 and into the biological tissue. As curved segment 41 exits applicator tool 10, curved segment will autonomously return to a curved configuration, which causes tip 44 to follow a curved path beneath the tissue surface. Due to the curved path, tip 44 exits the tissue surface and loops back toward attachment ring 30. Attachment ring 30 includes features that clamp and/or trap tip 44. As tip 44 exits the tissue surface, annular surface 718 (FIGS. 7 and 8) on engagement device 700 may help guide tip 44 toward attachment ring 30.

Figure 10:
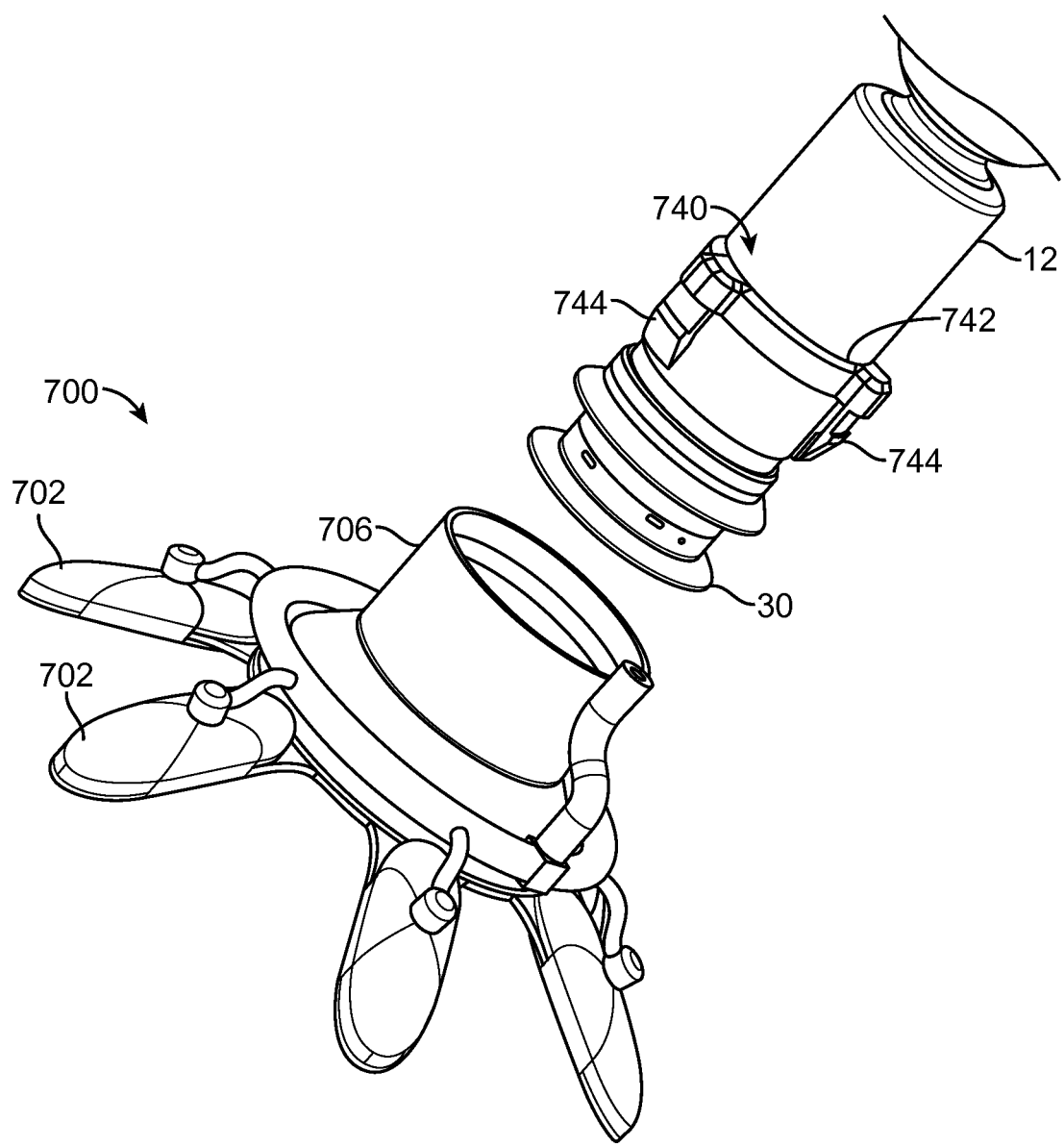
FIG. 10 is a perspective view of the engagement device of FIG. 1, showing the engagement device detached from the applicator tool having a connection device.
Figure 11:
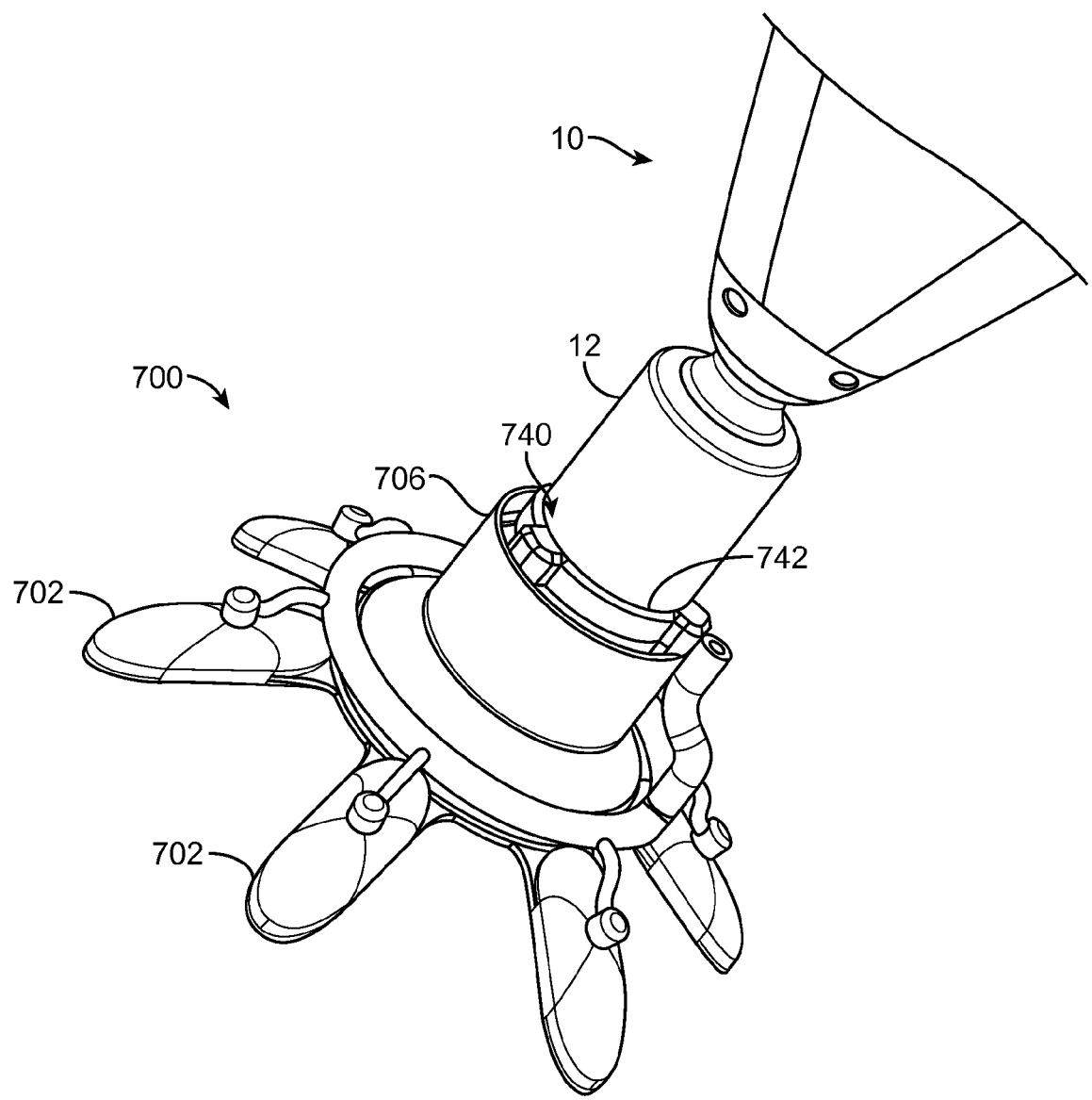
FIG. 11 is a perspective view of the engagement device of FIG. 1, showing the engagement device secured to the applicator tool by the connection device.

FIGS. 10 and 11 show connector 740 for connecting engagement device 800 to forward segment 12 of applicator tool 10. Connector 740 includes a circular band 742 that wraps around forward segment 12. Barbed arms 744 protrude axially from band 742 and are configured to engage a ring feature within coupling member 706 of engagement device 800. When connector 740 engages and retains engagement device 700, attachment ring 300 is at the appropriate position relative to the suction provided by contact members 702 during use. As will be discussed below, the relative position of attachment ring 300 and contact members 702 is controlled so that force loading of the heart tissue does not damage the tissue while allowing clips to be properly deployed.

In some embodiments, band 742 of connector 740 is fixedly attached to forward segment 12 of applicator tool 10 with no ability to adjust the axial position of contact members 702 of engagement device 700 relative to forward segment 12 and attaching ring 30. In other embodiments, band 742 is slideably attached to forward segment 12 to allow a medial practitioner to selectively adjust and fix the axial position of contact members 702 relative to forward segment 12 and attachment ring 30.

Figure 12:
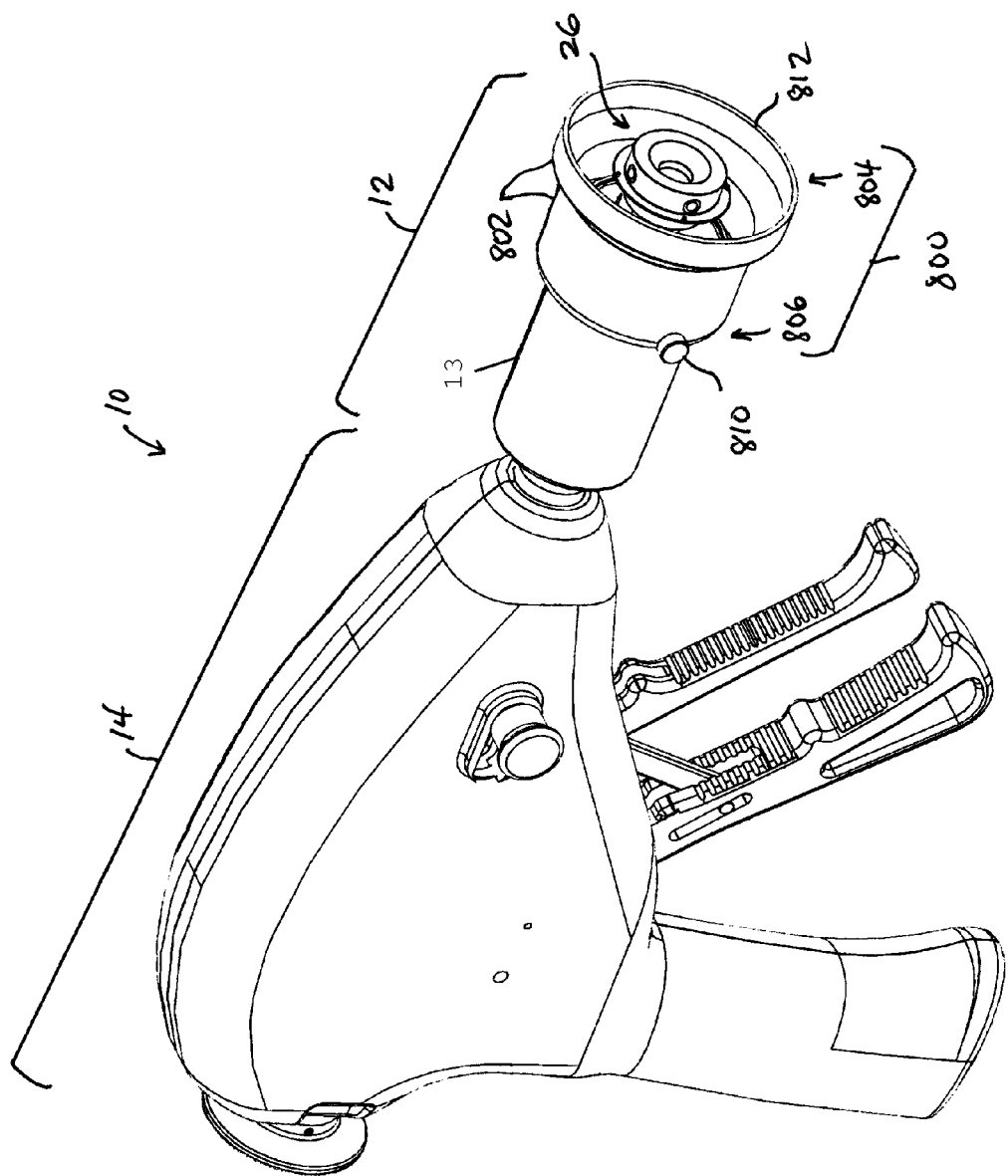
FIG. 12 is another coupling system for securing for securing an anastomotic prosthesis to biological tissue, showing the applicator tool of FIG. 1 with another engagement device.
Figure 13:
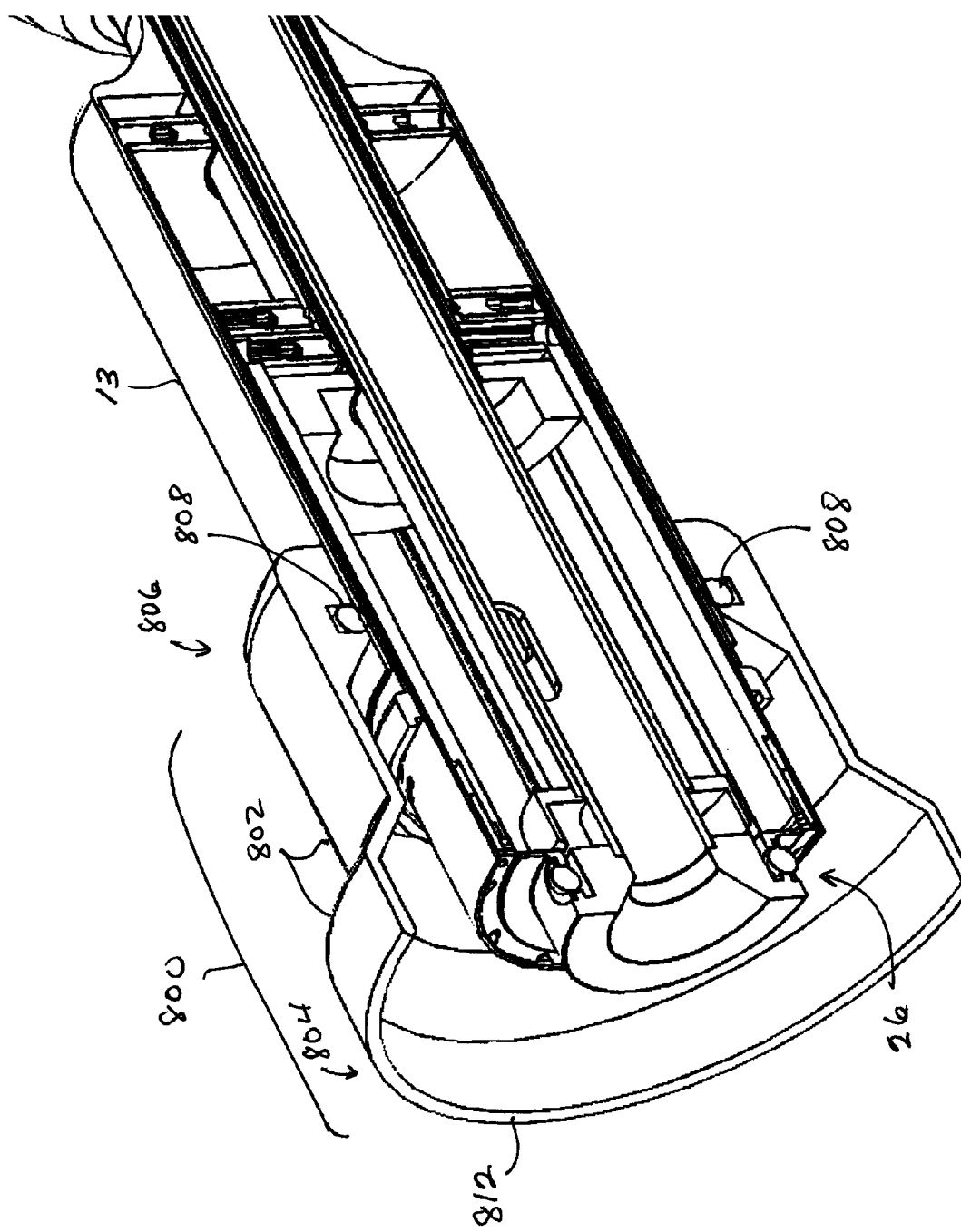
FIG. 13 is a detailed cross-section view of a forward portion of the coupling system of FIG. 12, showing the applicator tool and engagement device in perspective.

FIGS. 12 and 13 show applicator tool 10 of FIG. 1 with engagement device 800. Engagement device 800 includes suction cap 802 configured to maintain suction over the surface of tissue. Suction cap 802 is tubular in shape and comprises forward end 804 and rear end 806. Rear end 806 is slideably coupled to forward segment 12 of applicator tool 10. O-ring gasket 808 maintains a substantially fluid-tight seal between suction cap 802 and outer surface 13 of applicator tool 10. Set screw 810 is located on suction cap 802 to selectively allow and prevent sliding of suction cap 802. The head of the set screw 810 is exposed while the tip of set screw 810 is disposed adjacent outer surface 13 of applicator tool 10.

In use, attachment ring 30 (not shown in FIGS. 12 and 13) is carried on connector mechanism 26 of applicator tool 10 and within suction cap 802. The user maneuvers applicator tool 10 so that forward edge 812 of suction cap 802 is placed on the tissue surface. Forward edge 812 is circular and has an inner diameter larger than the outer diameter of attachment ring 30. Forward edge 812 is configured to seal against biological tissue to maintain negative pressure and suction within the interior cavity of suction cap 802. To accommodate a variety of possible curvatures in the biological tissue, the user may slide suction cap 802 axially on forward segment 12 of applicator tool 10 so that attachment ring 30 and forward edge 812 of suction cap 802 simultaneously contact the tissue surface. When suction cap 802 is at the desired axial position on forward segment 12, the user can manipulate the screw head so that the tip of set screw 810 presses against forward segment 12 and locks the position of suction cap 802. The user can apply a vacuum or suction through applicator tool 10 to produce negative pressure within the interior cavity of suction cap 802. With the negative pressure, forward edge 812 of suction cap 802 engages the tissue surface and prevents or minimizes relative movement between applicator tool 10 and the tissue surface. Since attachment ring 30 is located within suction cap 802, the tissue surface directly below attachment ring 30 is held in place against attachment ring 30.

In other embodiments, engagement device 800 is combined with all the features of engagement device 700 such that coupling member 706 is replaced by suction cap 802. Alternatively, coupling member 706 can be fitted over and attached onto suction cap 802. Suction can be applied to contact members 702 and/or suction cap 802 to engage applicator tool 10 to tissue. Applying suction to contact members 702 helps to stabilize areas of tissue spaced apart from and surrounding attachment ring 30. Applying suction to suction cap 802 helps to stabilize areas of tissue directly beneath attachment ring 30. While negative pressure is generated within contact members 702 and/or suction cap 802, clips 36 are deployed out of applicator tool 10 and into the underlying tissue.

During a surgical procedure, engagement device 700, 800 and applicator tool 10 are fixed to each other. Applicator tool 10 is hand held by the surgeon who manipulates controls on the applicator tool. As the surgeon places applicator tool 10 at the target tissue, engagement device 700, 800 will engage surrounding tissue with application of suction and thereby prevent or minimize relative movement between applicator tool 10 and the target tissue. Engagement device 700, 800 is not fixedly connected to a surgical bed, sternum retractor, or other stationary structure. Engagement device 700, 800 does not fix or stabilize the surrounding tissue relative to a stationary structure. Engagement device 700, 800 fixes or stabilizes the surrounding tissue relative to applicator tool 10, which moves under the direction of the clinician. Thus, after engagement device 700, 800 attaches to surrounding tissue with suction, and if the clinician manually moves applicator tool 10 left, right, up or down within the patient's body cavity, applicator tool 10 will remain stationary relative to the target tissue. Applicator tool 10 will also remain at the target tissue even if the target tissue moves due to pulsatile blood flow, unexpected change in the patient's body position, or other reason. Thus it will be understood that applicator tool 10 and engagement device 700, 800 are designed to move with the target tissue and not to slip relative to the target tissue. Engagement device 700, 800 enables applicator tool 10 to be "stuck" with the target tissue, which helps to deploy the clips at the precise location selected by the surgeon. If desired, suction can be partially decreased or completely removed to allow the surgeon to adjust the position of applicator tool 10 on the tissue.

As discussed above, negative pressure or suction is applied to the engagement device 700, 800 so that engagement device 700, 800 attaches to the target tissue. A particular amount of negative pressure is necessary for the purpose of deploying the clips with consistency from applicator tool 10. Inconsistent clip deployment may take the form of undue variation in depth, direction, and/or curvature in the path of travel of the clips. The amount of negative pressure needed for consistent clip deployment may depend on multiple factors, including but not limited to the number of clips being deployed, the type of tissue into which the clips are being deployed, and the size of the surface area to which vacuum is being applied. A method according to the invention can include the steps discussed above in combination with either one or both of (1) the step of selecting or determining an amount of negative pressure that corresponds to a threshold level of security between the applicator tool and the target tissue, and (2) the step of applying the preselected or predetermined amount of negative pressure to the engagement device 700, 800 during clip deployment. In various embodiments, the determined amount of negative pressure is selected to be below a maximum threshold. The maximum threshold may be selected to reduce the risk of injury to the target tissue.

Engagement device 700, 800 can be used for locating and targeting the site for attaching a VAD inflow conduit during an off-pump, minimally invasive surgical procedure as opposed to a conventional, open heart procedure. The term "off-pump" means that clip deployment is performed while the heart is beating and without a heart-lung or cardiopulmonary bypass procedure being performed. For example and without limitation, applicator tool 10 and engagement device 700, 800 can be introduced into the chest cavity of a patient via an intercostal approach or via a small incision between the ribs of the patient. In this example, a sternotomy and spreading of the left and right rib cage apart are avoided. After introduction into the chest cavity, the clinician can place applicator tool 10 on the ventricular apex of the heart (the target tissue) and apply a sufficient amount of negative pressure to engagement device 700, 800 that substantially prevents relative movement between the target tissue and applicator tool 10.

Engagement device 700, 800 applies preset or adjustable force loading between the applicator tool 10 and the tissue. This loading is important for the success of deploying the clips. When applicator tool 10 is used in concert with engagement device 700, 800, and as a vacuum is applied, applicator tool 10 is pressed downward (as a result of the suction) against the tissue. The downward force (also referred to as load) applied by applicator tool 10 on the tissue depends upon a connection device that connects engagement device 700, 800 and applicator tool 10 together. The exemplary connection device allows for control of the amount of force on the tissue so that the force is simultaneously (1) below a maximum level that would damage the tissue, and (2) at or above a minimum level needed to ensure that the clips are properly deployed without undue variation in depth, direction, and/or curvature in the path of travel of the clips. Control of the amount of force on the tissue can be accomplished by adjusting the distance between the forward tip of attachment ring 30 and the base (736 in FIG. 14, or 812 of FIG. 12) of engagement device 700, 800. The amount of force is increased when the attachment ring 300 is placed at a greater distance distal to or in front of the base of engagement device 700, 800. The connection device, for adjusting the distance, can include connector 740 (FIGS. 10 and 11) and/or screw 810 (FIG. 12).

Engagement device 700, 800 keeps the deployment site clear of possible obstruction. Engagement device 700, 800 completely engages the tissue area required for clip deployment and prevents surrounding tissue and other surgical devices from entering into that tissue area and interfering with clip deployment.

Engagement device 700 has contact members 702 that function as individual pods or feet that provide suction to discrete areas of tissue surrounding a central area into which clips are deployed. The central area is referred to as the clip deployment site. The discrete areas of tissue can be separated from each other by areas of tissue which receive no suction. Engagement device 800 has suction cap 802 that provides suction to a circular area that includes the clip deployment site.

As shown in FIG. 6, each contact member 702 has peripheral edge 705 that forms the boundary of a suction port or opening. In various embodiments, each contact member has a peripheral edge shaped and configured to improve sealing for applying suction. The suction openings face inward toward central axis 730 of engagement device 700. Contact members 702 can be symmetrically arranged around central axis 730. In use, the suction openings face inward toward attachment ring 30 (not shown in FIG. 6). As shown in the partial, cross-sectional diagram of FIG. 14, suction openings face inward toward clip deployment site 732 and are oriented at acute Angle A1 relative to central axis 730. Due to Angle A1, the suction openings of contact members 702, as a group, create a frustoconical shape or a cup shape that rests on the curved outer surface of the ventricular apex of the heart during a surgical procedure.

Figure 14:
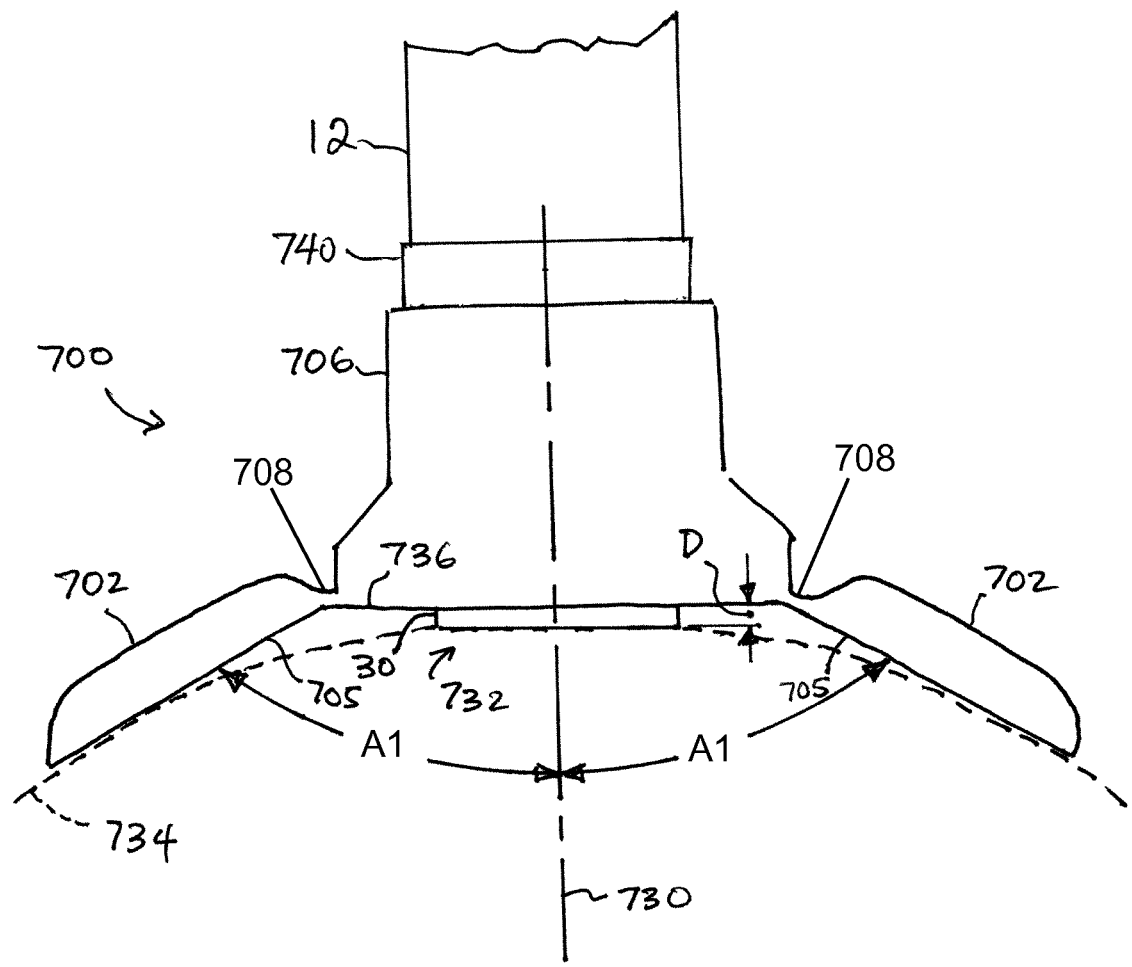
FIG. 14 is a side, cross-section view of the engagement device and applicator tool of FIG. 11.

As shown in FIG. 14, contact members 702 extend radially outward and in a forward direction from base 736 of coupling member 706 of attachment device 700. Attachment device 700 is secured to forward segment 12 of applicator tool 10 such that attachment ring 30, which is held by forward segment 12, protrudes in a forward direction from base 736 by Axial Distance D. Attachment device 700 is secured to forward segment 12 such that, during clip deployment, Axial Distance D results in a loading force on the heart tissue that is simultaneously (1) below a maximum level that would damage the tissue, and (2) at or above a minimum level needed to ensure that the clips are properly deployed without undue variation in depth, direction, and/or curvature in the path of travel of the clips. In other embodiments, attachment ring 30 is level with base 736 during clip deployment. In other embodiments, attachment ring 30 is located below base 736 so as to be recessed within coupling member 706 during clip deployment.

The orientation and shape of the suction ports serve multiple purposes. Angle A1 is selected to allow for easy attachment of engagement device 700 to the heart. Angle A1 allows engagement device 700 to conform to the curved outer surface 734 of the heart. Angle A1 can be within the range of about 10 degrees to about 80 degrees, or more narrowly within the range of about 20 degrees to about 70 degrees, or at about 60 degrees. The appropriate angle depends in part on the physical size of the patient's heart. A relatively small angle would be more suitable for the curved outer surface of a relatively small heart, and a relatively large angle would be more suitable for the curved outer surface of a relatively large heart.

The orientation and shape of the suction openings will remodel the clip deployment site for engagement with applicator tool 10 and attachment ring 30. The configuration of the suction openings will pull the heart tissue 734 up to form an ideal shape for engagement with applicator tool 10 and attachment ring 30. The slanted angle of the engagement device surface in contact with the heart tissue 734, in combination with the vacuum suction, will change the shape of the heart so it can conform to that of the engagement device and/or attachment ring 30.

The orientation and shape of the suction openings minimize the movement of the tissue during clip deployment.

The angular orientation of the suction opening, Angle A1, can be adjusted according to the surgeon's need. Contact members 702 are adjustable and designed to contour to the shape of the outer surface of the heart. Making joint 708 (FIG. 6) from a flexible and elastic material allows for adjustment.

Figure 15:
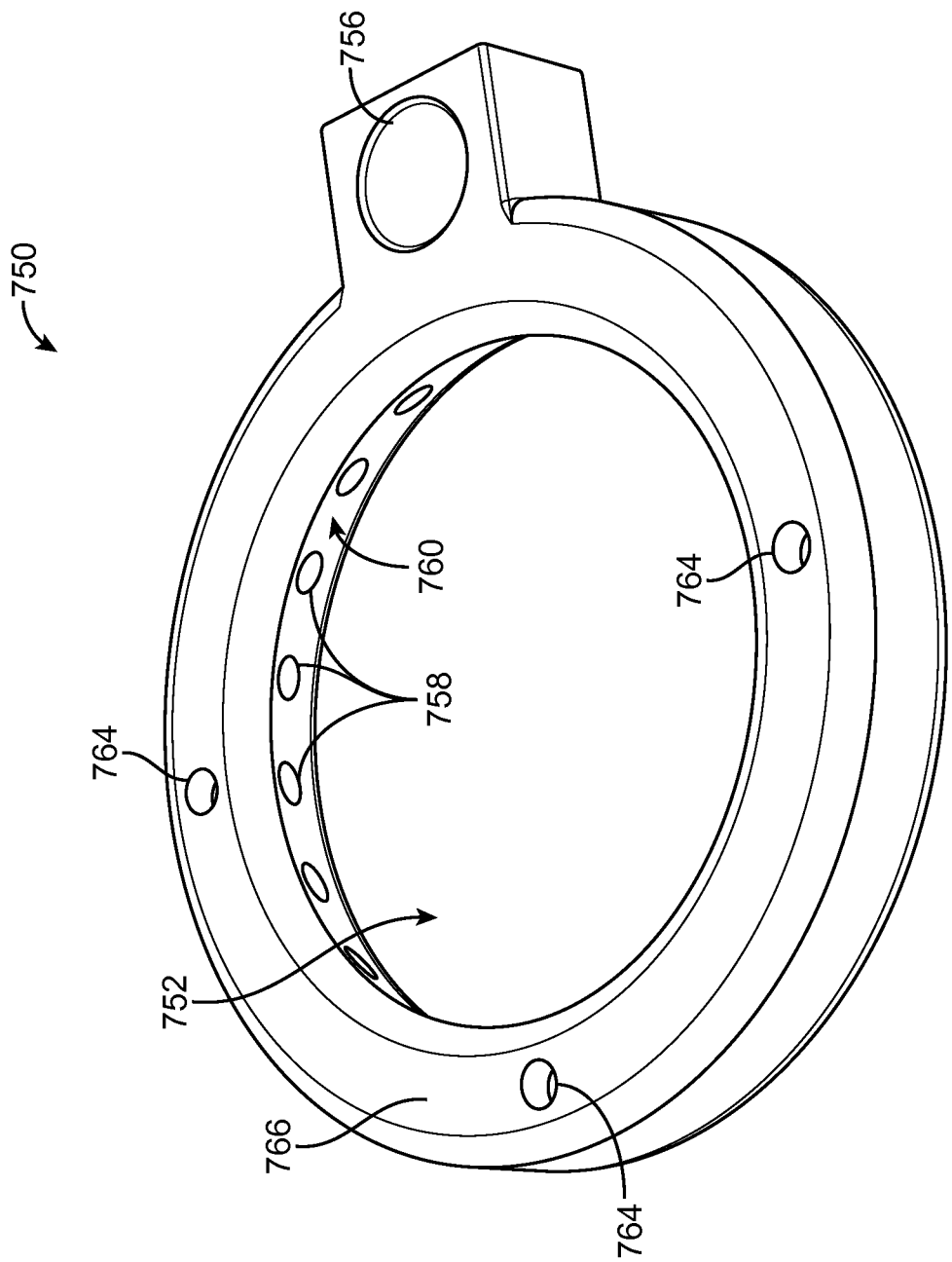
FIGS. 15 and 16 are perspective and cross-section views of an exemplary ring-shaped contact member for use with the devices of FIGS. 1 and 12, showing a frustoconical contact surface.
Figure 16:
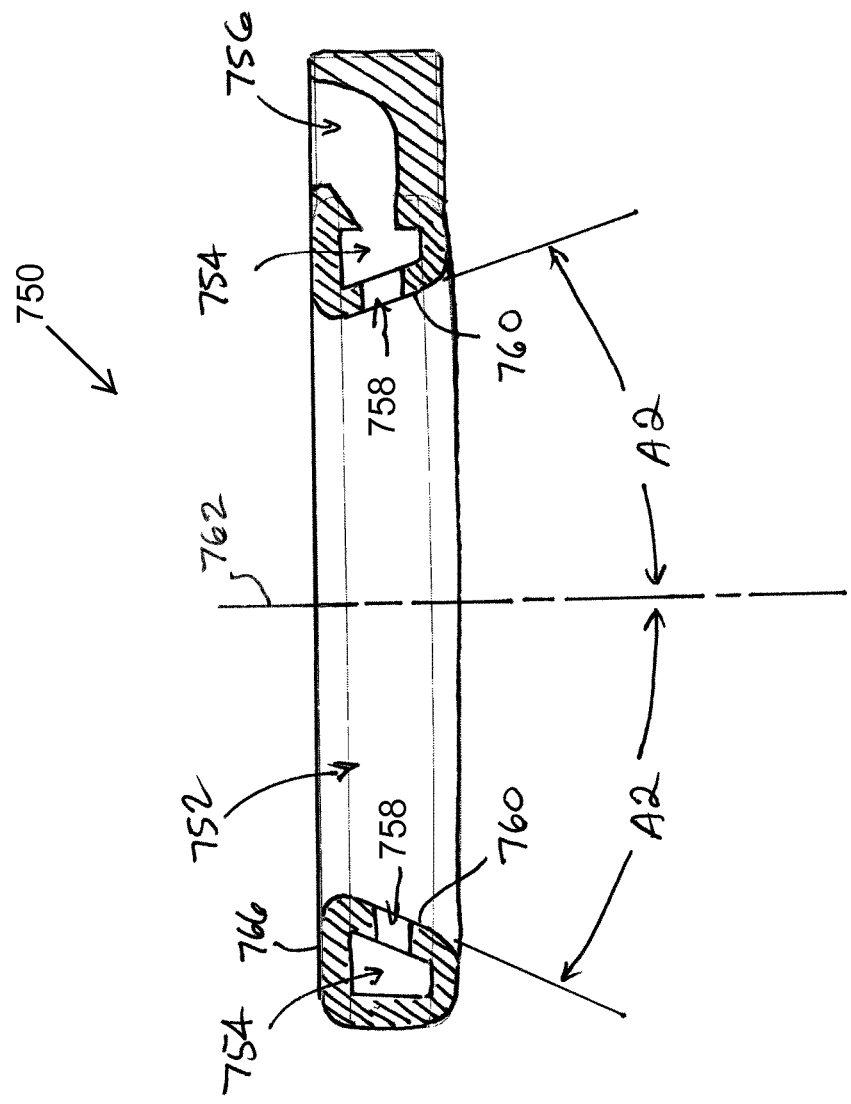

An engagement device can have an annular or ring-shaped contact member 750, as shown in FIGS. 15 and 16. Ring-shaped contact member 750 can be implemented as an alternative to or in combination with contact members 702 and/or suction cap 802. Contact member 750 is hollow and substantially circular, with a central opening 752 sized to receive coupling member 706 (FIG. 2) of the engagement device and attachment ring 30 carried by applicator tool 10. An interior air passageway 754 encircles central opening 752. Passageway 754 is in fluid communication with outlet port 756 and a plurality of inlet ports, also referred to as suction openings 758. Air is drawn out of passageway 754 from outlet port 756. Outlet port 756 can be connected to a vacuum source, such as rear tube 704a in FIG. 3. Air is drawn into passageway 754 from suction openings 758, which are configured to apply suction to heart tissue. Suction openings 758 are spaced apart from each other and are circumferentially distributed around central opening 752. Suction openings 758 are formed into interior surface 760 of contact member 750. In various embodiments, interior surface 760 is frustoconical in shape. The exemplary interior surface faces radially inward toward central opening 752 and central axis 762 of contact member 750.

Interior surface 760 is oriented at acute Angle A2 relative to central axis 762. Angle A2 can be about 25 degrees. In other embodiments, Angle A2 can be within the range of about 10 degrees to about 80 degrees, or more narrowly within the range of about 20 degrees to about 70 degrees, or at about 60 degrees. Angle A2 is selected with the purpose of maintaining contact with the heart surface which is not flat, but curved so that ring-shaped contact member 750 can "cup" the heart.

Contact member 750 includes multiple attachment points 764 (FIG. 15) on an exterior, rearward facing surface 766. Attachment points 764 allow contact member 750 to be retained and secured by a connector on forward segment 12 of applicator tool 10. The connector can be the same as or similar to connector 740 described above in connection with FIGS. 10 and 11.

Figure 17:
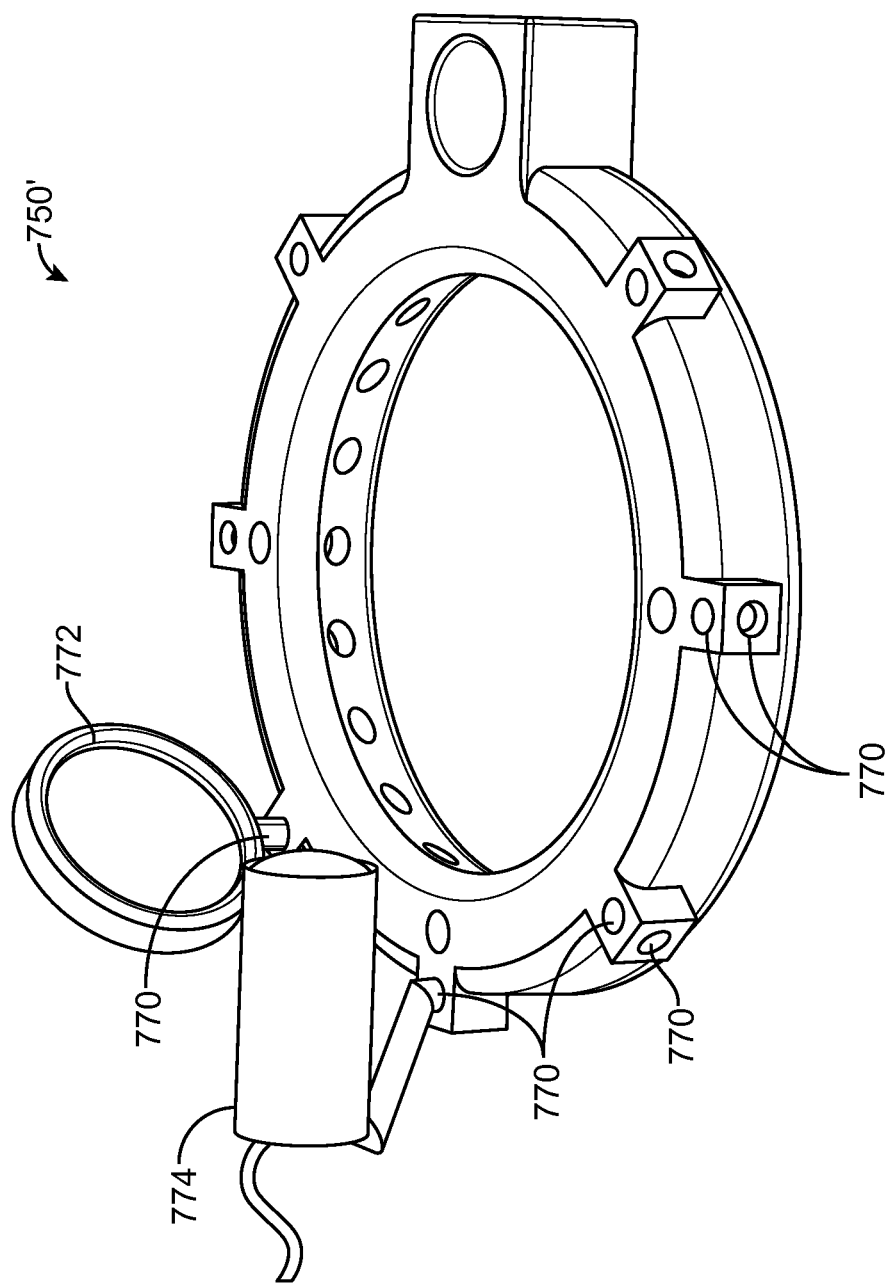
FIG. 17 is a perspective view of an exemplary ring-shaped contact member for use with the devices of FIGS. 1 and 12, showing accessory attachment points.

As shown in FIG. 17, ring-shaped contact member 750' includes a plurality of accessory attachment points 770, in addition to all the features for contact member 750 of FIGS. 15 and 16. Accessory attachment points 770 are configured to receive and retain accessories, including without limitation adjustable mirror 772 and adjustable light 774 for improving visibility during a surgical procedure. Accessory attachment points 770 are distributed circumferentially to allow a variety of mounting positions for the accessories.

In other embodiments, engagement device 700, 800 has attachment points around the outer perimeter of the device. The attachment points are configured to receive and retain add-on devices, such as a viewing port or a light source. The attachment points can be the same as or similar to accessory attachment points 770 described in connection with FIG. 17.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for connecting an anastomotic prosthesis to tissue, the method comprising:
applying suction to an engagement device attached to an applicator tool, the applicator tool configured to deploy a securement into an anastomotic prosthesis and tissue; and
deploying the securement into the anastomotic prosthesis and the tissue during the applying of the suction to the engagement device,
wherein the applying of the suction inhibits or prevents relative movement between the applicator tool and the tissue,
wherein the anastomotic prosthesis is an attachment ring for connecting an artificial conduit to a hollow anatomical organ, and the method further comprises positioning the attachment ring on the hollow anatomical organ before applying the suction to the engagement device and while the attachment ring is mounted on the applicator tool, and the method further comprises releasing the attachment ring from the applicator tool after the deploying of the securement.

2. The method of claim 1, further comprising removing the suction from the engagement device after the deploying of the securement, wherein the applying of the suction causes the engagement device to engage the tissue, and the removing of the suction causes the engagement device to disengage the tissue.

3. The method of claim 1, wherein the applying of the suction to the engagement device includes applying the suction to a plurality of contact members disposed on the tissue, each contact member including a suction opening and a joint, and the method further comprises flexing the joints to adjust angular orientations of the suction openings.

4. The method of claim 3, wherein each contact member includes a concave wall, the concave wall has an aperture, and the suction is applied through a fluid conduit coupled to the apertures.

5. The method of claim 3, further comprising placing a forward segment of the applicator tool in a coupling member, the contact members being attached to the coupling member.

6. The method of claim 5, further comprising adjusting an axial position of the contact members by sliding the coupling member on the forward segment of the applicator tool.

7. The method of claim 1, further comprising connecting an inflow conduit of a ventricular assist device to the attachment ring.

8. The method of claim 1, wherein the securement is a clip having a sharp tip for piercing the tissue.

9. A method for connecting an anastomotic prosthesis to tissue, the method comprising:
applying suction to an engagement device attached to an applicator tool, the applicator tool configured to deploy a securement into an anastomotic prosthesis and tissue; and
deploying the securement into the anastomotic prosthesis and the tissue during the applying of the suction to the engagement device,
wherein the applying of the suction inhibits or prevents relative movement between the applicator tool and the tissue, and
wherein the applying of the suction to the engagement device includes applying the suction to a plurality of contact members disposed on the tissue, each contact member including a suction opening and a joint, and the method further comprises flexing the joints to adjust angular orientations of the suction openings.

10. The method of claim 9, wherein each contact member includes a concave wall, the concave wall has an aperture, and the suction is applied through a fluid conduit coupled to the apertures.

11. The method of claim 9, further comprising placing a forward segment of the applicator tool in a coupling member, the contact members being attached to the coupling member.

12. The method of claim 11, further comprising adjusting an axial position of the contact members by sliding the coupling member on the forward segment of the applicator tool.

* * * * *